United States Patent [19]

Gravener

[11] Patent Number: 5,772,099
[45] Date of Patent: Jun. 30, 1998

[54] SURGICAL FASTENING APPARATUS WITH ALIGNMENT PIN

[75] Inventor: Roy D. Gravener, Fairfield, Conn.

[73] Assignee: United States Surgical Corporation, Norwalk, Conn.

[21] Appl. No.: 625,150

[22] Filed: Apr. 1, 1996

[51] Int. Cl.⁶ .................................................. A61B 17/068
[52] U.S. Cl. ............................................ 227/176.1; 227/19
[58] Field of Search ........................... 227/175.1, 176.1, 227/178.1, 180.1, 19, 1.19

[56] References Cited

U.S. PATENT DOCUMENTS

| | | |
|---|---|---|
| 4,591,085 | 5/1986 | Di Giovanni . |
| 4,605,004 | 8/1986 | Di Giovanni et al. . |
| 4,633,874 | 1/1987 | Chow et al. . |
| 4,715,520 | 12/1987 | Roehr, Jr. et al. . |
| 5,071,052 | 12/1991 | Rodak et al. . |
| 5,219,111 | 6/1993 | Bilotti et al. . |
| 5,285,944 | 2/1994 | Green et al. . |
| 5,364,001 | 11/1994 | Bryan . |
| 5,397,046 | 3/1995 | Savage et al. . |
| 5,413,268 | 5/1995 | Green et al. . |
| 5,425,745 | 6/1995 | Green et al. . |
| 5,458,279 | 10/1995 | Plyley . |
| 5,465,894 | 11/1995 | Clark et al. ............................... 227/19 |
| 5,470,006 | 11/1995 | Rodak ...................................... 227/19 |
| 5,476,206 | 12/1995 | Green et al. . |
| 5,487,499 | 1/1996 | Sorrentino et al. . |
| 5,529,235 | 6/1996 | Boiarski et al. .......................... 227/19 |
| 5,605,273 | 2/1997 | Hamblin et al. .......................... 227/19 |
| 5,607,094 | 3/1997 | Clark et al. ............................... 227/19 |
| 5,632,432 | 5/1997 | Schulze et al. .......................... 227/19 |

FOREIGN PATENT DOCUMENTS 125867  6/1967  U.S.S.R. .

Primary Examiner—Scott A. Smith

[57] ABSTRACT

An apparatus for applying surgical fasteners to body tissue includes an alignment pin assembly having an alignment pin and a corresponding retainer. In a preferred embodiment the alignment pin has a flange with a tissue abutment surface and a circumferential detent. The retainer is preferably a ring shaped member having a tissue abutment surface and which engages with the alignment. The pin and retainer are releasably held in proximity to the distal end of the apparatus within one or the other of the cartridge or anvil member of the apparatus and are simultaneously engaged with each other and applied to body tissue upon firing of the apparatus. Visual inspection of the body tissue after the operation provides an indication as to whether the apparatus was properly aligned during firing.

14 Claims, 5 Drawing Sheets

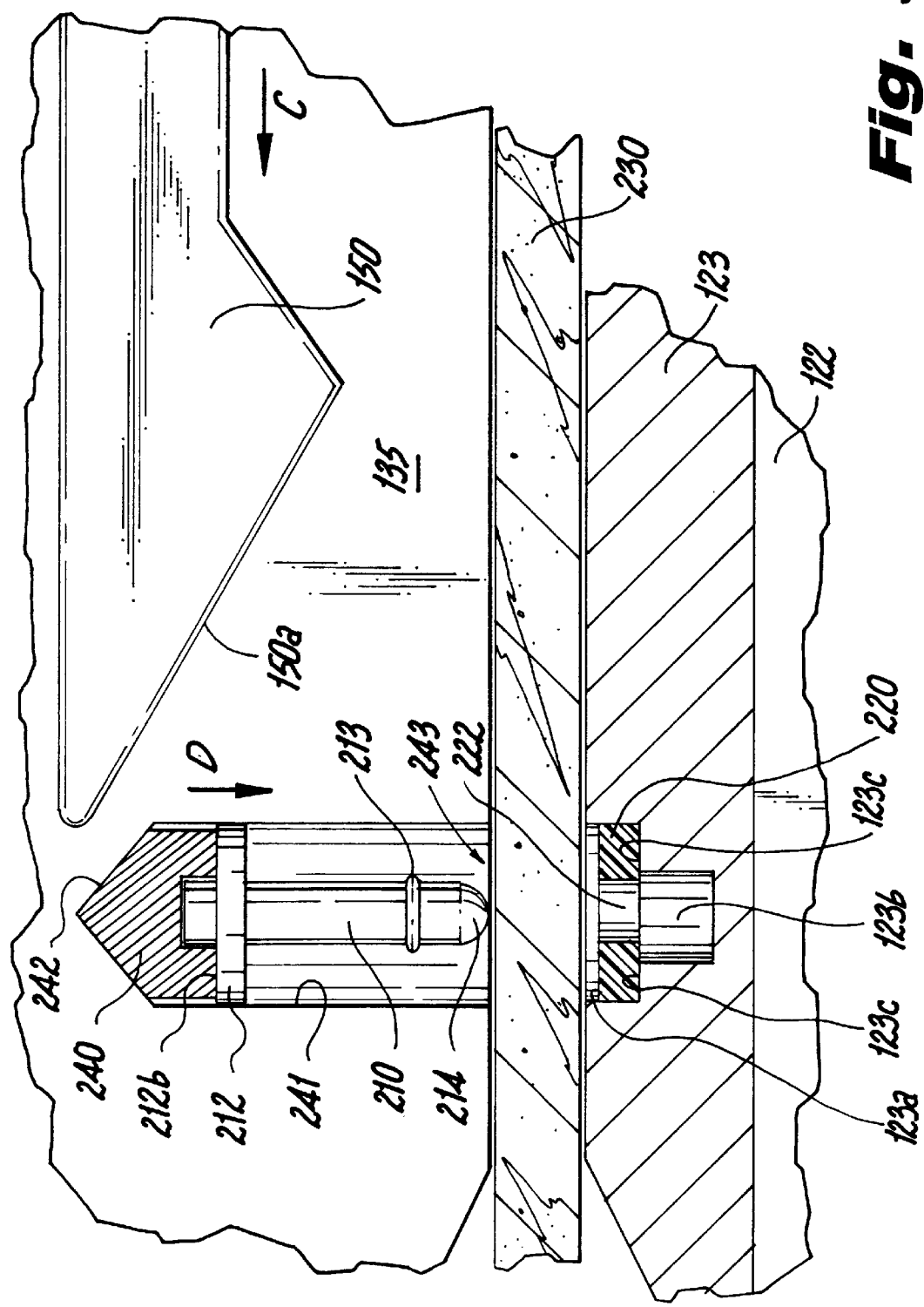

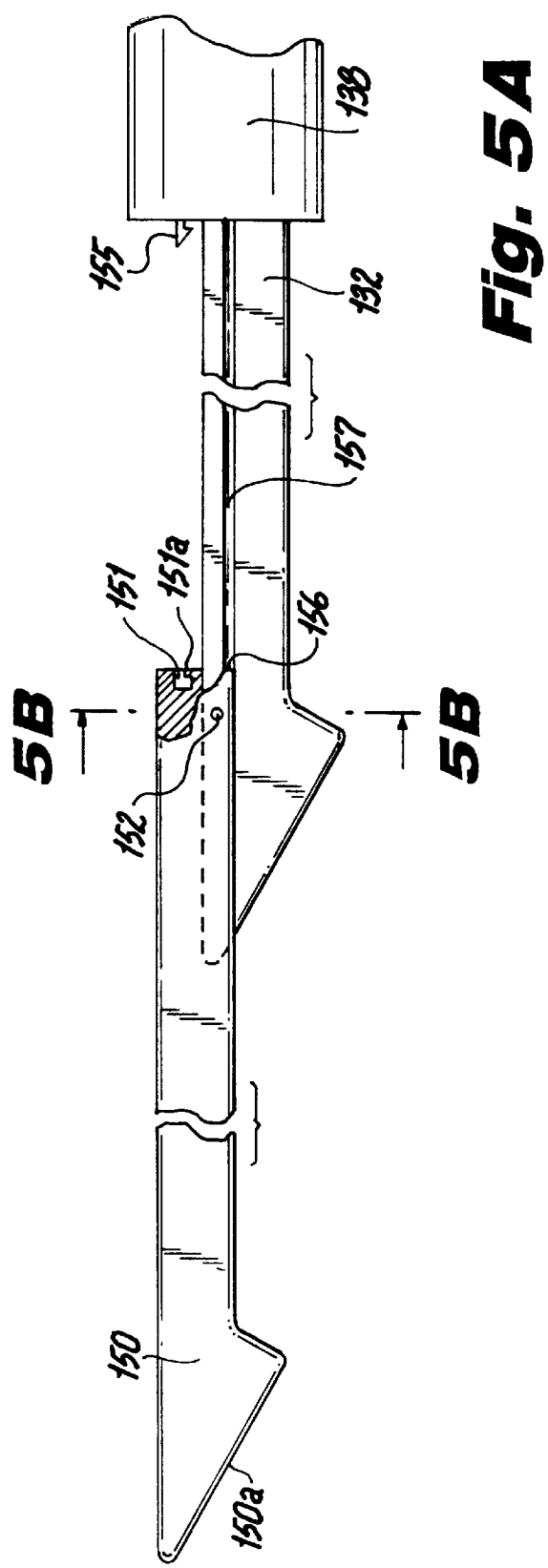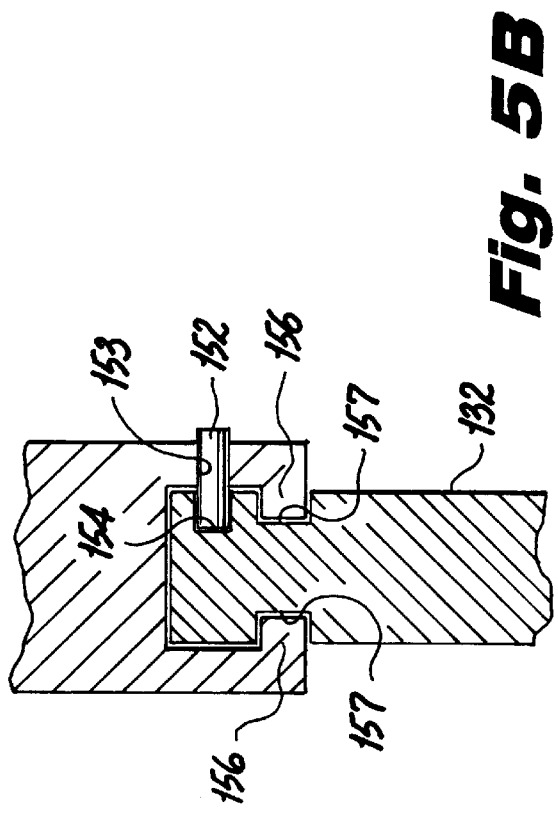

SURGICAL FASTENING APPARATUS WITH ALIGNMENT PIN

BACKGROUND OF THE INVENTION

1. Field of the Invention

The present invention relates to an apparatus for sequentially applying a plurality of surgical fasteners to body tissue, and more particularly to a surgical stapler for resection, transection, and creation of anastomoses.

2. Background of the Art

Surgical fastening apparatus for resection, transection and creation of anastomoses are known in the art. For example, such apparatus are commonly used for suturing gastric and intestinal walls with spaced parallel rows of longitudinally aligned surgical fasteners or staples and are described in various patents.

For example, U.S. Pat. No. 3,079,606 to Bobrov et al. discloses an instrument for suturing gastric and intestinal walls with metal staples by inserting the tips of the instrument through apertures in the walls of the organs to be sutured. The apparatus includes a two-part frame with each part having a finger-like projection or fork. The forks are inserted respectively into the apertures in the walls of the organs to be sutured. The frame parts are hinged together with the body tissue held between the forks. When the instrument is actuated, or "fired", longitudinally moving cam bars contact staple drive members in one of the forks, thereby pushing the surgical staples through the body tissue and into an anvil in the opposite fork by which they are crimped closed. A knife blade between the cam bars creates an incision between the parallel rows of staples. It should be noted, however, that the knife blade is an optional feature, ie. the instrument may be used to fasten body tissue without creating an incision between the rows of staples.

U.S. Pat. No. 3,490,675 to Green et al. discloses an improvement on the instrument discussed above, whereby a double row of staples is placed on each side of the incision.

A further improvement in this type of instrument is disclosed in U.S. Pat. No. 3,499,591 to Green, which incorporates an improved structure for the staple carrying cartridge, a pusher assembly which includes the cam bars and the knife, and staple drive members, each of which is capable of driving more than one staple.

Generally, the above mentioned instruments are successfully used in abdominal, gynecological, pediatric and thoracic surgery for resection, transection, and creation of anastomoses. Surgical fastener applying apparatus can be used to apply metal staples, which are criped in the anvil portion of the apparatus, or bioabsorbable fasteners, such as two-part fasteners having a fastener portion and a retainer which interlocks therewith upon firing of the instrument. In any such instrument it is important to maintain proper alignment of the jaws of the instrument, and positioning of the tissue held between the jaws.

Alignment of the instrument jaws insures that the surgical fasteners are properly closed. In the case of metal staples, the staples are closed when their legs are crimed in corresponding depressions in the anvil With respect to the two-part fasteners, the fastener portions must be properly aligned with the corresponding retainer portions of the anvil assembly so that closure, or interlocking can be achieved.

Proper tissue positioning insures that the instrument operates on the proper area of tissue. Such instruments, of course, are employed on various thicknesses of tissue. However, thinner tissue may have a tendency to shift within the closed instrument. The possibility of tissue shifting is increased by the presence of body fluids, such as blood, which tends to make the tissue slippery. On the other hand, an instrument whose jaws close firmly on thin tissue to prevent its movement might pinch the tissue, particularly thicker tissue.

One method which has been employed to preserve alignment of the instrument jaws is to use positioning buttons or projections on the lateral edges of the cartridge. These projections guide the anvil portion into proper alignment with the staple cartridge when the jaws of the instrument are closed Under some circumstances, however, such projections can act as pinch points of tissue.

An improvement over the positioning buttons or projections is described in U.S. Pat. No. 5,014,899 to Presty et al. wherein a resilient deflectable arm with a projection frictionally engages the body tissue and exerts a biasing force on the tissue to hold the tissue in position.

SUMMARY OF THE INVENTION

A surgical apparatus for sequentially applying a plurality of surgical fasteners to body tissue is provided herein. The apparatus comprises: a) holding means for holding a plurality of surgical fasteners in at least two parallel rows oriented along a lengthwise axis of the apparatus; b) anvil means for closing the fasteners; c) drive means movable along the lengthwise axis of the apparatus between a proximal position and a distal position for sequentially driving the fasteners from the holding means and against the anvil means to effect closure of the fasteners; and, d) alignment means located distally to the rows of fasteners for facilitating and indicating alignment between the holding means and the anvil means, the alignment means comprising at least one pin slidably mounted within a slot in one of the holding means or the anvil means and movable into engagement with an aperture in the other of the holding means or the anvil means in response to movement of the drive means from the proximal position toward the distal position.

The surgical fasteners can be metal staples or two-part fasteners fabricated from a bioabsorbable material Also, the alignment means can be fabricated from a bioabsorbable material. Suitable bioabsorbable materials include polymers of glycolide, lactide, caprolactone, p-dioxanone, trimethylene carbonate and the like, and chemical and physical combinations thereof.

The alignment means can further comprise a retainer ring having an aperture for receiving the pin, and a tissue abutment surface, the retainer ring being releasably positioned within the aperture in the other of the holding means or the anvil means.

In a preferred embodiment, the pin comprises a shaft having a rear end and a tissue piercing forward tip, a flange projecting circumferentially from the shaft in the vicinity of the rear end thereof, the flange having a forwardly facing tissue abutment surface, and interference means such as a circumferential detent located in the vicinity of the forward tip and spaced apart from the flange. The pin and the retainer are movable relative to each other from a non-engaged position wherein the pin and the retainer are spaced apart from each other, and a fully engaged position wherein the retainer is engaged with the pin such that the shaft is disposed through the aperture of the retainer and the detent is located forward of the retainer.

The circumferential detent is configured to offer less resistance to relative movement of the pin and the retainer from the non-gaged position into the fully engaged position than to disengagement of the pin and the retainer from the fully engaged position to the non-engaged position. In an alternative embodiment the detent comprises a sloped forward surface and a rear surface substantially perpendicular to the axial orientation of the shaft Also provided herein is a method for verifying alignment of the above mentioned apparatus. The method comprises (a) providing the aforementioned apparatus (b) positioning body tissue between the fastener holding means and the anvil means and clamping the tissue therebetween; (c) actuating the apparatus such that the alignment means facilitates alignment between the anvil means and the fastener holding means.

BRIEF DESCRIPTION OF THE DRAWINGS

Preferred embodiments of the invention are described hereinbelow, wherein:

FIGS. 5, 5A and 5b are partly sectional elevational view-of the alignment pin assembly mounted within the apparatus;

DETAILED DESCRIPTION OF THE PREFERRED EMBODIMENTS

Figure 1:
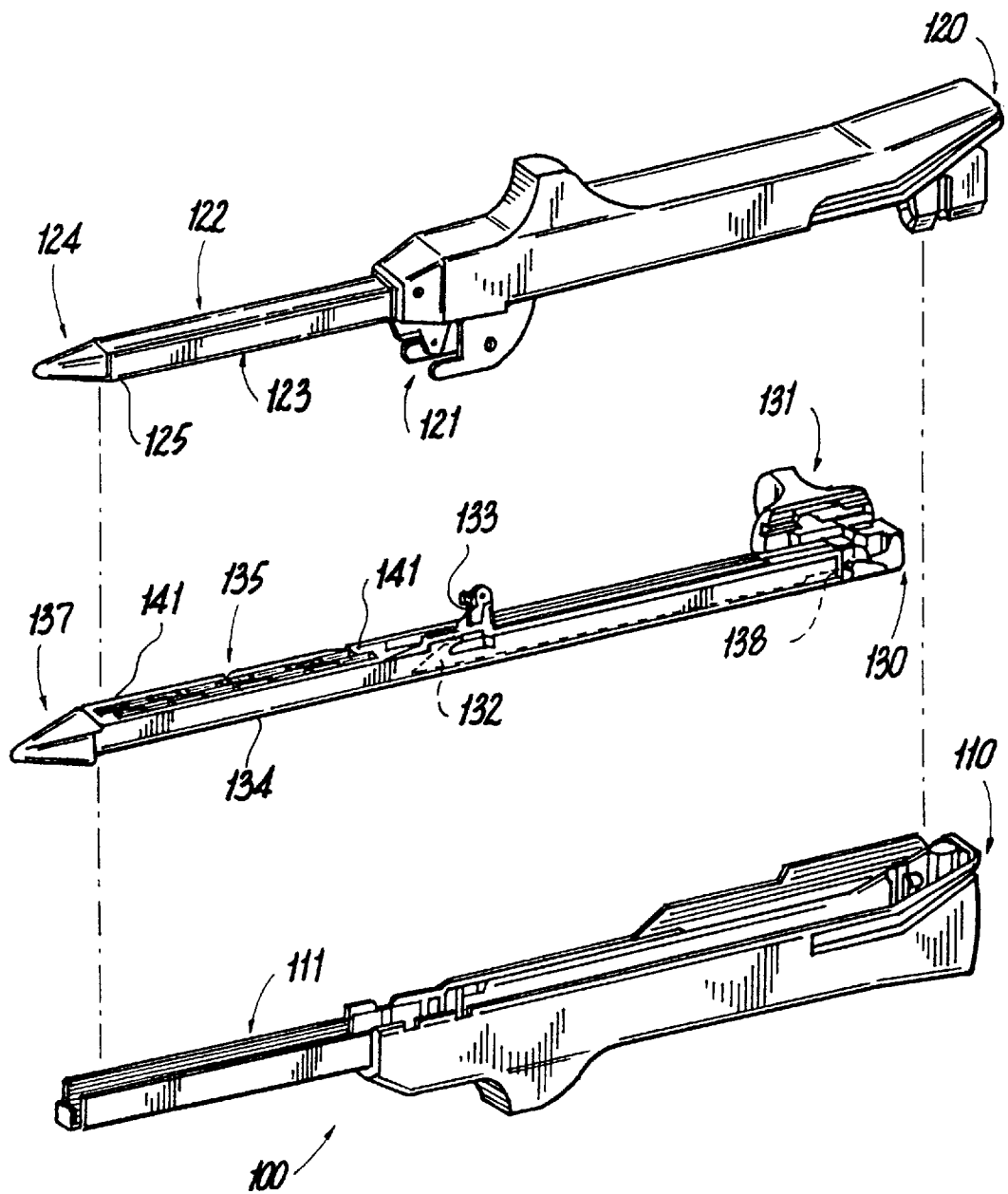
FIG. 1 is an exploded perspective view with parts separated of a surgical stapling apparatus.

Referring to FIG. 1, the surgical stapling apparatus 100 of the present invention comprises a first frame 110 having a distal finger-like projection 111 for holding a cartridge assembly. A second frame 120 has a pair of hinge plates 121 for hingedly connecting to the first frame 110, and a distal finger-like projection 122 for carrying an anvil assembly 123. The anvil assembly 123 is formed of a plate with indentations or depressions for crimping the legs of metal staples. Alternatively, the anvil assembly may include means for holding rows of retainer portions of two-part surgical fasteners to facilitate mutual engagement of the fastener and retainer portions of the two-part fasteners. More details about such surgical stapling apparatus employing metal staples or polymeric two-part fasteners may be found, for example, in U.S. Pat. Nos. 5,156,614, 5,156,315, 4,863,088, 4,633,874, 4,633,861, 4,520,817, 3,499,591, 3,490,675, and 3,079,606, all of which are herein incorporated by reference. Tip 124 allows distal projection 122 to be more easily positioned in body tissue.

Actuating assembly 130 for driving the surgical fasteners is a replaceable insert which includes a pusher assembly having a thrust knob 131, cam bars 132, cam bar retainer 138, and knife blade 133. The actuating assembly or insert 130 further includes a stationary carrier 134 for holding cartridge assembly 135. Tip 137 at the distal end of the cartridge assembly facilitates positioning body tissue for fastening.

Figure 2:
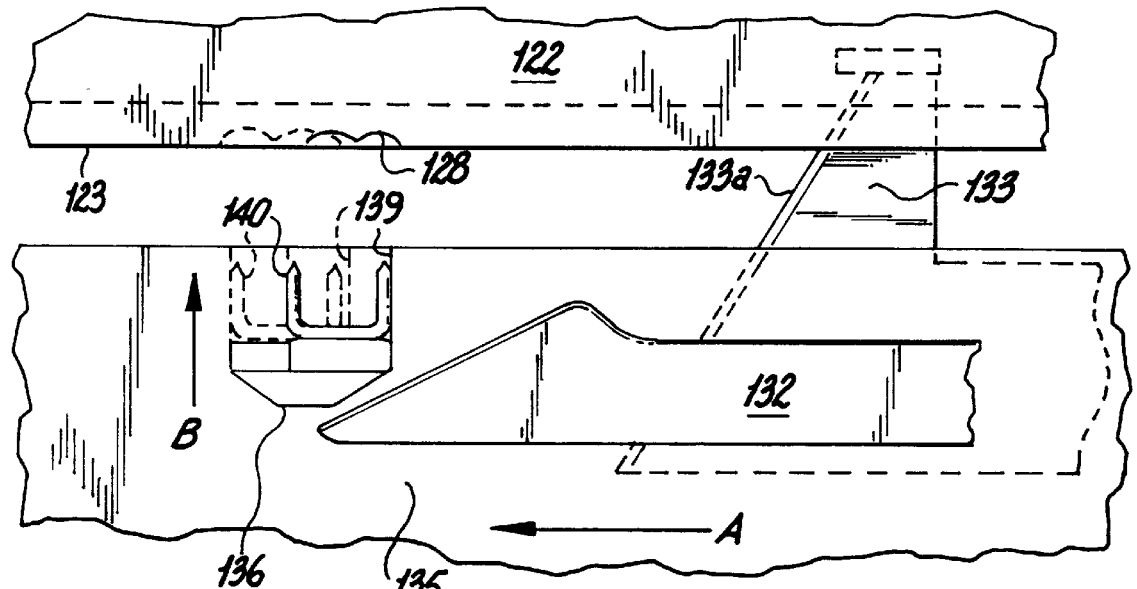
FIG. 2 is a elevational view illustrating a portion of the cartridge assembly.

Referring also to FIG. 2, cartridge assembly 135 includes pusher members 136 for pushing surgical fasteners out from their respective slots and into contact with the anvil for closure. Cam bars 132 and knife 133 are mounted at their proximal ends to cam bar retainer 138 (FIG. 1), which is connected to the thrust knob 131 and which provides a means for transferring manually applied force from the thrust knob 131 to the cam bars 132.

In operation, the assembly 130 is loaded into the first frame 110, and the instrument is then assembled such that the body tissue to be operated upon is located between the cartridge assembly 135 and the anvil assembly 123. The knife 133 is positioned such that it can simultaneously move along slot 126 (FIG. 3) in the anvil and slot 141 (FIG. 1) in the cartridge assembly. The instrument is then fired by the surgeon's pressing forward (ie. distally) on the thrust knob 131.

Referring again to FIG. 2, the cam bars 132 and knife 133 are then moved distally and longitudinally along the instrument in the direction indicated by arrow A. The knife 133 creates an incision in the body tissue (not shown) by means of its distal cutting edge 133a, and the cam bars 132 drive the fastener pusher 136 in a direction indicated by arrow B, which is transverse to that of the longitudinal axis of the instrument. The pushers 136, in turn, drive the fasteners 140 out of their slots 139 and into the depressions 128 in the anvil plate for crimping, thereby fastening the tissue on both sides of the incision. When the operation is completed the used replaceable insert 130 can be disposed, and a new one installed in the apparatus.

Figure 3:
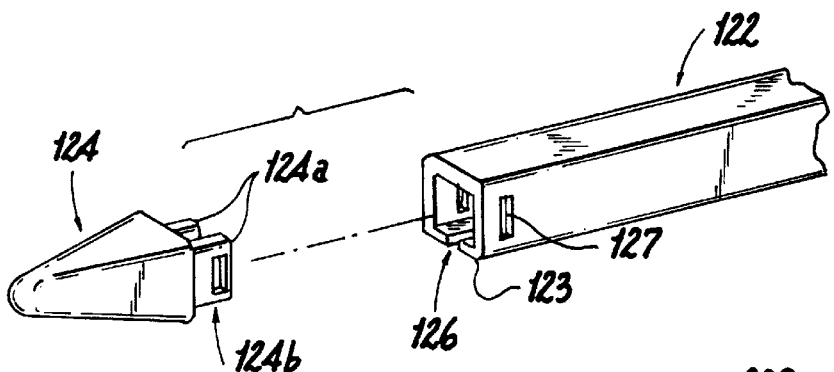
FIG. 3 is an exploded perspective view of the anvil portion of the instrument.

FIG. 3 illustrates the anvil tip 124 having prongs 124a and detents 124b on the outer sides of the prongs. The detents 124b are for engaging side slots 127 in the distal projection 122. Distal projection 122 carries an anvil assembly which can simply comprise an anvil plate 123 with depressions 128 for crimping the legs of staples. Alternatively, the anvil assembly can house the retainer portions of two-part bioabsorbable surgical fasteners and means for releasably holding them until they are engaged with their respective fastener portions.

Figure 4:
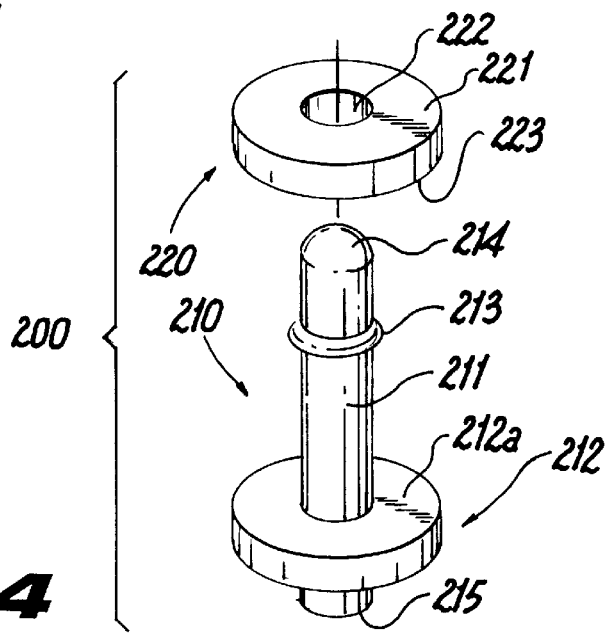
FIG. 4 is an exploded perspective view of the alignment pin assembly.

Referring to FIG. 4, the alignment pin assembly 200 of the present invention includes a pin member 210 and a retainer member 220, and is preferably fabricated from a bioabsorbable polymer such as polymers of glycolide, lactide, p-dioxanone, caprolactone, trimethylene carbonate and the like, and chemical and physical combinations thereof. Structurall, pin 210 is a single piece and includes a longitudinal shaft portion 211 having a forward tissue piercing tip 214, and a rear end 215, a flange 212 having a tissue abutment surface 212a, and interference means such as a circumferential detent 213. The retainer 220 is preferably a ring shaped member 221 having a central aperture 222 for receiving shaft 211 of the pin 210 and a planar tissue contacting surface 223. The diameter of aperture 222 is at least as large as that of the shaft 211, but is slightly smaller than the outer diameter of the circumferential detent 213.

Figure 6:
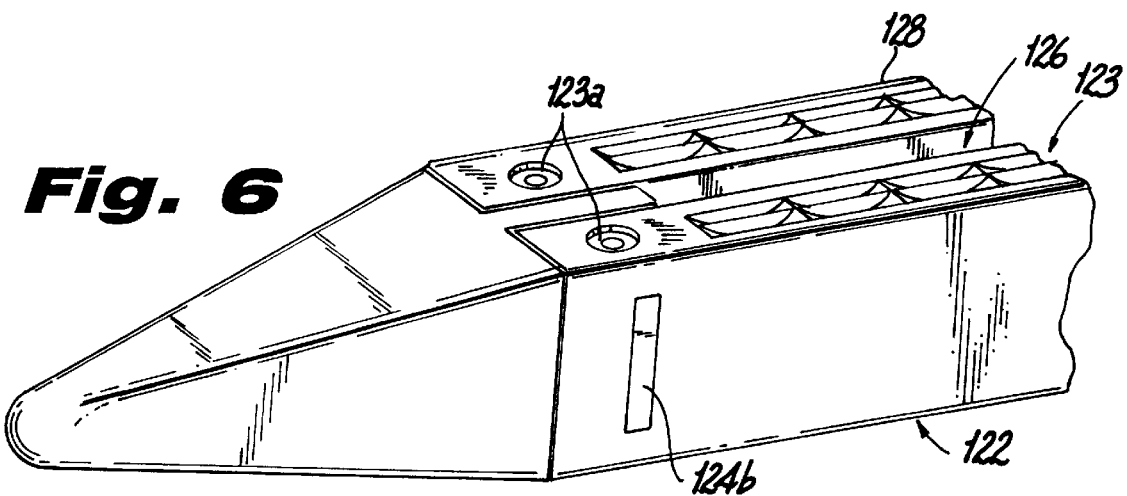
FIG. 6 is a perspective view of the anvil portion of the instrument containing two retainer members.

Referring to FIGS. 5 and 6, the alignment pin assembly 200 is initially positioned in the stapler apparatus 100 such that one member of the assembly is in the cartridge assembly 135 and the other member is in the anvil 123 or anvil tip 124. As illustrated by way of exemplification of an optional but preferred embodiment, pin member 210 is slidably positioned within slot 241 of the cartridge assembly 135 and is oriented so that forward end 214 points toward the anvil. A pusher element 240 is located behind the rear portion of the pin and contacts the rear surface 212b of the flange 212.

The retainer member 220 is positioned within circular slot 123a near the distal end of the anvil. More than one alignment pin assembly may be used, as shown in FIG. 6 wherein two circular slots 123a are incorporated into the anvil surface 123. The circular slot 123 preferably has a lower portion 123b of lesser diameter and annular ledge 123c for supporting the retainer member 220. Slot 123a is positioned in alignment with corresponding slot 241 to maintain shaft 211 of the pin member 210 in alignment with aperture 222 of the retainer 220. Both the retainer 220 and pin 210 are slidably within their respective slots, but are configured and dimensioned so as to be held by a frictional fit therein until the pushing force upon actuation of the instrument overcomes the friction and drives the pin 210 and retainer together.

FIG. 5 illustrates actuation of the instrument. The cam bar extension 150 moves longitudinally upon actuation towards the distal end of the cartridge as shown by arrow C. The edge 150a of the cam bar extension contacts the camming surface 242 of pusher element 240 thereby driving pusher element in the direction of arrow D through slot 241 and pushing the pin member 210 out of the opening 243 of the slot, through body tissue 230 and into and through aperture 222 of the retainer until full engagement of the alignment pin 210 and retainer 220 is achieved, ie. circumferential detent 213 passes fully through aperture 222 to the opposite side of the retainer. Even though the outer diameter of the circumferential detent 213 is slightly larger than the diameter of aperture 222, the resilience and flexibility of the material from which the alignment pin assembly 200 is fabricated, allows enough "give" or bending under the forces applied during firing of the apparatus to permit passage of the detent 213 through aperture 222.

Figure 8:
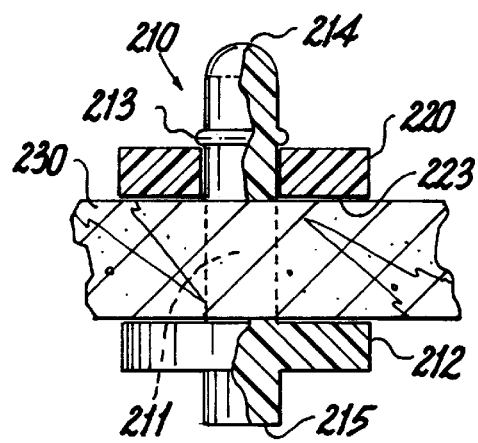
FIG. 8 is a partly sectional elevational view of the alignment pin assembly affixed to body tissue.

Referring to FIG. 8, the circumferential detent may have an arcuate surface defining a generally semicircular cross section as seen in detent 213.

Figure 7:
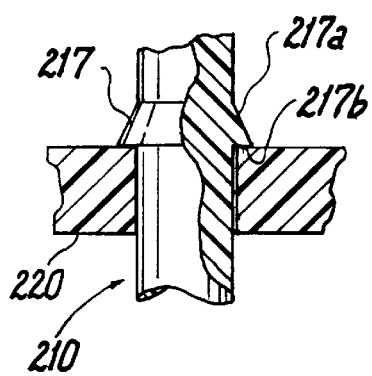
FIG. 7 is a partly sectional elevational view of an alternative embodiment of the alignment pin in conjunction with a retainer member.

Referring to FIG. 7, the circumferential detent may be optionally shaped like a wedge 217 wherein detent 217 includes forward sloped surface 217a and a back stop surface 217b perpendicular to the axial orientation of the shaft 211. The sloped surface 217a facilitates passage of the pin 210 through the retainer 220 until full engagement is achieved. The stop surface 217b offers proportionately greater resistance to subsequent disengagement The alignment pin 210 is actuated before the staples are fired. The actuation of the alignment pin is accomplished by the same actuating force that applies the staples (i.e. pushing on the thrust knob). Thus, the present invention includes an extension of the cam bar distal to the portion of the cam bar which drives the staple pushers. The distal extension is used to drive the alignment pin pusher. Since it is located near the distal end of the apparatus and reaches the distal end before the cam bar assembly fully fires the staples, the extension is releasable.

As can be seen in FIGS. 5A and 5B cam bar extension 150 is an elongated member having a distal camming surface 150a for camming the alignment pin pusher 240. Cam bar extension 150 is slidably mounted to the cam bar 132. Inward pointing projections 156 of the cam bar extension 150 engage longitudinal slots 157 of the cam bar 132. Initially, the cam bar extension 150 is held to a fixed location with respect to the cam bar 132 by means of a pin 152 which is transversely disposed through aperture 153 in the cam bar extension 150 and in aperture 154 of the cam bar 132. The pin 152 is fabricated from a soft polymeric material which shears when a predetermined magnitude of force is applied to fire the apparatus. Thus, when the cam bar retainer 138 is pushed distally to fire the fasteners, the cam bar extension 150 is advanced to drive the alignment pin pusher 240 to actuate the alignment pin 210 at the distal end portion of the apparatus. The cam bar extension 150 shortly thereafter reaches the end of the apparatus and can advance no further. The user of the apparatus continues to press forward on the thrust knob 131 but with greater force, thereby causing the pin 152 to shear and permitting the cam bar 132 to advance distally to fire the fasteners while the cam bar extension 150 remains stationary. When the cam bar retainer 138 reaches the proximal end of the cam extension 150 (after the cam bar 132 has fired all of the fasteners) distally projecting hook 155 on the distal face of the cam bar retainer 138 enters into proximal aperture 151 of the cam bar extension 150 and resiliently snaps into engagement with lip portion 151a. When the thrust knob 131 and cam bar retainer 138 are drawn back into the initial pre-firing position the cam bar extension 150 is also drawn back.

After the instrument is fully fired, the pin 210 and joined retainer 20 are fastened to the body tissue 230. Upon removing of the jaws of the instrument alignment pin 210 and the retainer 220 disengage from their respective slots. The body tissue 230 is released with the alignment pin assembly 200 attached thereto as shown in FIG. 8.

The alignment pin assembly 200 of the present invention provides important advantages. Misalignment of the jaws of the instrument tends to be greater at the distal end of the instrument than in the middle. The alignment pin assembly helps to ensure that the distal end of the instrument is in proper alignment Hence, the alignment pin assembly facilitates proper alignment of the instrument jaws. Moreover, presence of the alignment pin assembly in the body tissue after the stapler is withdrawn from the tissue gives the surgeon visual confirmation that the staples were in alignment with the anvil when fired and were properly closed. To facilitate visual observation, the alignment pin assembly may be fabricated from synthetic polymer to which appropriate biocompatible dyes have been added to give the alignment pin assembly a distinctive color which will stand out vividly against the color of the body tissue.

In yet another embodiment of the invention an alignment pin is slidably positioned within the cartridge and, upon initiation of the firing action of the apparatus is moved into engagement with the anvil.

Figure 9:
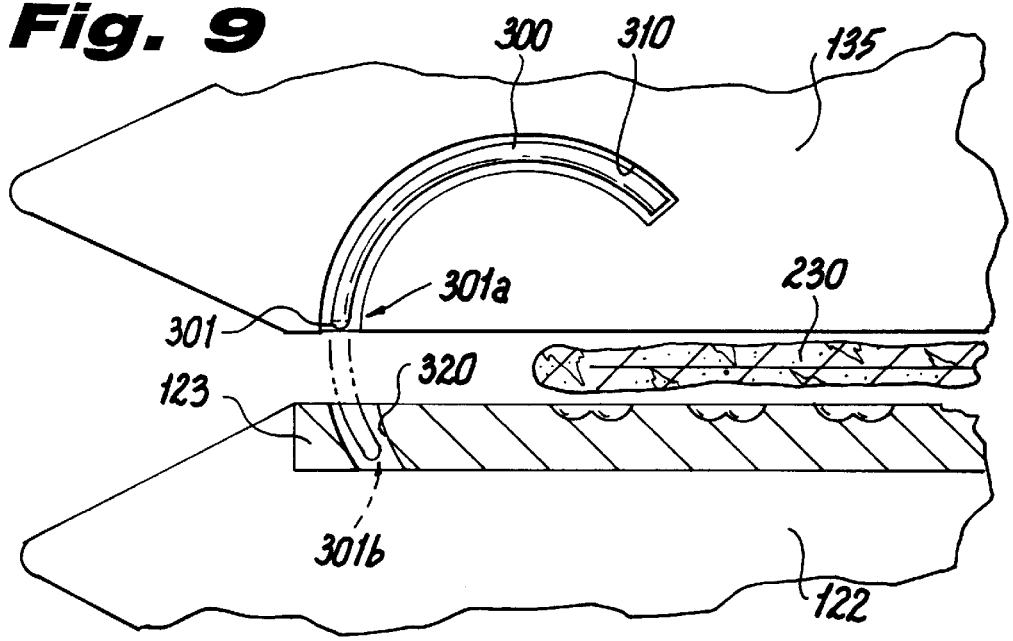
FIG. 9 is a diagrammatic view illustrating an alternative embodiment of the present invention employing a retractable alignment pin.

Referring to FIG. 9 in an alternative embodiment alignment pin 300 comprises a retractable curvilinear shaft slidably positioned within curved slot 310 in stapler cartridge 135. The distal or forward end 301 of the pin 300 is initially positioned within slot 310 at position 301a such that it does not protrude into the gap between anvil 122 and cartridge 135. Upon initiation of the firing action of the apparatus, the forward end 301 is moved to position 301b wherein it engages aperture 320 of the anvil. Once the engagement is completed alignment of the catridge 135 and anvil 122 is verified and improved. This embodiment is preferably employed when the tissue 230 being operated upon does not extend beyond the line of staples. The alignment pin 300 is preferably withdrawn completely back into the cartridge 135 to its original position after the firing stroke is complete. This is accomplished by providing a lost motion feature, e.g., slot, as part of the extension arm which actuates pin 300 such that pin 300 is advanced into position 301(b) as firing begins, and withdrawn from position 301(*b*) at the final portion of return movement of the cam bar adapter. The fastener applying apparatus is then opened, and the tissue released. Alignment pin 300 is preferably fabricated from a biologically compatible metal, such as stainless steel.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A surgical apparatus for sequentially applying a plurality of surgical fasteners to body tissue, which comprises:
   a) holding means for holding a plurality of surgical fasteners in at least two parallel rows oriented along a lengthwise axis of the apparatus;
   b) anvil means for closing said fasteners;
   c) drive means movable along said lengthwise axis of the apparatus between a proximal position and a distal position for sequentially driving said fasteners from said holding means and into contact with said anvil means to effect closure of said fasteners; and,
   d) alignment means located distally to said rows of fasteners for facilitating and indicating alignment between said holding means and said anvil means, said alignment means comprising at least one pin slidably mounted within a slot in one of said holding means or said anvil means and movable into engagement with an aperture in the other of said holding means or said anvil means in response to movement of said drive means from said proximal position toward said distal position.

2. The apparatus of claim 1 wherein said surgical fasteners are metal staples.

3. The apparatus of claim 1 wherein said surgical fasteners comprise two-part fasteners fabricated from a bioabsorbable material.

4. The apparatus of claim 1 wherein said drive means comprises a cam bar.

5. The apparatus of claim 1 wherein said alignment means is fabricated from a bioabsorbable material.

6. The apparatus of claim 5 wherein said bioabsorbable material is selected from the group consisting of polymers of glycolide, lactide, caprolactone, p-dioxanone, and chemical and physical combinations thereof.

7. The apparatus of claim 5 wherein said alignment means further comprises a retainer ring having an aperture for receiving said at least one pin, and a tissue abutment surface, said retainer ring being releasably positioned within said aperture in said the other of said holding means or said anvil means.

8. The apparatus of claim 7 wherein said at least one pin comprises a shaft having a rear end and a forward tip, a flange projecting circumferentially from said shaft in the vicinity of the rear end thereof, said flange having a forwardly facing tissue abutment surface, and a circumferential detent located in the vicinity of said forward tip and spaced apart from said flange.

9. The apparatus of claim 8 wherein said at least one pin and said retainer are movable relative to each other from a non-engaged position wherein said at least one pin and said retainer are spaced apart from each other, and a fully engaged position wherein said retainer is engaged with said at least one pin such that said shaft is disposed through said aperture of said retainer and said detent is located forward of said retainer.

10. The apparatus of claim 9 wherein said at least one circumferential detent is configured to offer less resistance to relative movement of said at least one pin and said retainer from said non-engaged position into said fully engaged position than to disengagement of said at least one pin and said retainer from said fully engaged position to said non-engaged position.

11. The apparatus of claim 8 wherein said detent comprises a sloped forward surface and a rear surface substantially perpendicular to the axial orientation of the shaft.

12. The apparatus of claim 1 wherein said holding means comprises a replaceable cartridge.

13. The apparatus of claim 7 wherein said at least one pin includes interference means for permitting engagement of said at least one pin with said retainer ring, and for resisting subsequent disengagement of said at least one pin and said retainer ring.

14. The apparatus of claim 13 wherein said interference means comprises a detent extending circumferentially around said at least one pin.

* * * * *